US012788220B2

(12) United States Patent
Patel et al.

(10) Patent No.: US 12,788,220 B2
(45) Date of Patent: Nov. 10, 2026

(54) ENDOSCOPY MASK WITH AIR FILTRATION

(71) Applicant: THE REGENTS OF THE UNIVERSITY OF CALIFORNIA, Oakland, CA (US)

(72) Inventors: Shiv Patel, Bellflower, CA (US); Philip Weissbrod, Encinitas, CA (US); Andrew Vahabzadeh-Hagh, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 738 days.

(21) Appl. No.: 18/251,537

(22) PCT Filed: Nov. 4, 2021

(86) PCT No.: PCT/US2021/058120
§ 371 (c)(1),
(2) Date: May 2, 2023

(87) PCT Pub. No.: WO2022/098915
PCT Pub. Date: May 12, 2022

(65) Prior Publication Data

US 2023/0404372 A1 Dec. 21, 2023

Related U.S. Application Data

(60) Provisional application No. 63/110,316, filed on Nov. 5, 2020.

(51) Int. Cl.
*A61B 1/00* (2006.01)
*A41D 13/11* (2006.01)
(Continued)

(52) U.S. Cl.
CPC .......... *A61B 1/00142* (2013.01); *A41D 13/11* (2013.01); *A61B 1/00154* (2013.01); *A61B 90/40* (2016.02); *A61M 16/06* (2013.01)

(58) Field of Classification Search
CPC . A61B 1/00142; A61B 1/00154; A61B 1/233; A61B 1/24; A61B 90/18;
(Continued)

(56) References Cited

U.S. PATENT DOCUMENTS

| | | | | |
|---|---|---|---|---|
| 3,357,426 A | | 12/1967 | Cohen | |
| 5,431,158 A | * | 7/1995 | Tirotta | A61M 16/0488 128/207.14 |

(Continued)

FOREIGN PATENT DOCUMENTS

| | | | | |
|---|---|---|---|---|
| CN | 201586310 U | * | 9/2010 | A61M 16/06 |
| CN | 210992441 U | * | 7/2020 | A61M 16/06 |
| WO | WO-2021214448 A1 | * | 10/2021 | A62B 23/025 |

OTHER PUBLICATIONS

3M Health Care, "Particulate Respirator & Surgical Mask 1860 Series", URL: https://www.3m.com/3M/en_US/p/d/b00038114/. Retrieved May 27, 2026. 3 pages.

(Continued)

*Primary Examiner* — Joseph D. Boecker
(74) *Attorney, Agent, or Firm* — Ashurst Perkins Coie US LLP

(57) ABSTRACT

Disclosed are a medical mask apparatus for use in medical procedures and methods of endoscopy. In one aspect, a medical mask apparatus includes a mask material conforming to a patients face along a sealing surface. The medical mask further includes a nose cone with a conically shaped first end and a cylindrically shaped second end, a cap that engages the second end of the nose cone through the mask material, wherein a portion of the mask material is captured at an interface between the nose cone and the cap. There is a valve in the cap, wherein the valve is flexible to expand and allow a medical instrument to pass through the valve. The medical mask also includes one or more attachment
(Continued)

straps to hold the medical mask apparatus on the patients face.

17 Claims, 9 Drawing Sheets

(51) Int. Cl.
*A61B 90/40* (2016.01)
*A61M 16/06* (2006.01)

(58) Field of Classification Search
CPC ..... A61B 90/40; A61B 5/6803; A61B 5/6819; A61B 5/682; A41D 13/11; A41D 13/1176; A61M 16/06; A61M 16/20; A61M 2025/022; A61M 2025/0226; A61M 2210/0618; A61M 2210/0625
See application file for complete search history.

(56) References Cited

U.S. PATENT DOCUMENTS

| | | | | |
|---|---|---|---|---|
| 9,272,108 | B2 | 3/2016 | Hu | |
| 2001/0012923 | A1 | 8/2001 | Christopher | |
| 2007/0199567 | A1 | 8/2007 | Kanzer | |
| 2017/0189635 | A1 | 7/2017 | Beard | |
| 2017/0197052 | A1 | 7/2017 | Tylka et al. | |
| 2022/0000575 | A1 * | 1/2022 | Ugbeye ............. | A41D 13/1138 |

OTHER PUBLICATIONS

Asadi, S., "Aerosol emission and superemission during human speech increase with voice loudness", Sci Rep. 2019;9(1):2348. doi:10.1038/s41598-019-38808-z, 10 pages.
Bann, D. V., "Impact of coronavirus (COVID-19) on otolaryngologic surgery: brief commentary", Head Neck. 2020; 42(6). doi:10.1002/hed.26162, pp. 1227-1234.
Bartoszko, J. J., "Medical masks vs N95 respirators for preventing COVID-19 in healthcare workers: a systematic review and meta-analysis of randomized trials", Influenza Other Respir Virus. 2020;14(4): doi:10.1111/irv.12745, pp. 365-373.
Bergman, M. S., "Correlation of respirator fit measured on human subjects and a static advanced headform", J Occup Environ Hyg. 2015;12(3). doi: 10.1080/15459624.2014.957832, pp. 163-171.
Bourouiba, L., "Violent expiratory events: on coughing and sneezing", J Fluid Mech. 2014;745:doi:10.1017/jfm.2014.88, pp. 537-563.
Canelli, R., "Barrier enclosure during endotracheal intubation", N Engl J Med. 2020;382(20): 1957-1958. doi:10.1056/NEJMc2007589, 2 pages.
Chua, H., ""Closed" supraglottic airway-guided intubation during the COVID-19 pandemic: a Glo germ follow-up", Anesth Analg. 2020;131. doi:10.1213/ANE.0000000000005032, pp. e168-e169.
Davies, J. C., "Nasal endoscopy during the COVID-19 pandemic: mitigating risk with 3D printed masks", The Laryngoscope. 2020;130: doi:10.1002/lary.29004, pp. 2561-2563.
Dugdale, C.M., "Filtration efficiency, effectiveness, and availability of N95 face masks for COVID-19 prevention", JAMA Intern Med. 2020;180. doi:10.1001/jamainternmed.2020.4218, pp. 1612-1613.
Feldman, O., "Exposure to a surrogate measure of contamination from simulated patients by emergency department personnel wearing personal protective equipment", JAMA. 2020;323(20). doi:10.1001/jama.2020.6633, pp. 2091-2093.
Fried, J., "Nasal endoscopy protocols in the era of COVID-19", World J Otorhinolaryngol Head Neck Surg. 2020; 6. doi:10.1016/j.wjorl.2020.04.007, pp. S33-S35.
Grossman, J., "Institution of a novel process for N95 respirator disinfection with vaporized hydrogen peroxide in the setting of the COVID-19 pandemic at a large academic medical center", J Am Coll Surg. 2020;231(2). doi:10.1016/j.jamcollsurg.2020.04.029, pp. 275-280.
Gupta, J. K., "Flow dynamics and characterization of a cough", Indoor Air. 2009;19(6). doi:10.1111/j.1600-0668.2009. 00619.x, pp. 517-525.
Han, Z. Y., "Characterizations of particle size distribution of the droplets exhaled by sneeze", J R Soc Interface. 2013; 10(88):20130560. doi:10.1098/rsif.2013.0560, 11 pages.
Hoffman, H. T., "Negative pressure face shield for flexible laryngoscopy in the COVID-19 era", Laryngoscope Investig Otolaryngol. 2020;5(4). doi:10.1002/lio2.437, pp. 718-726.
ISA/US, "International Search Report and Written Opinion", Application No. PCT/US2021/058120. Mail Date: Feb. 3, 2022. 10 pages.
Khoury, T., "Aerosolized particle reduction: a novel cadaveric model and a negative airway pressure respirator (NAPR) system to protect health care workers from COVID-19", Otolaryngol Head Neck Surg. 2020;163(1). doi:10.1177/0194599820929275, pp. 151-155.
Kim, H., "Assessing real-time performances of N95 respirators for health care workers by simulated workplace protection factors", Ind Health. 2015;53(6). doi: 10.2486/indhealth.2014-0259, pp. 553-561.
Kowalski, L. P., "COVID-19 pandemic: effects and evidence-based recommendations for otolaryngology and head and neck surgery practice", Head Neck. 2020;42(6): doi: 10.1002/hed.26164, pp. 1259-1267.
Kwon, J. H., "Assessment of healthcare worker protocol deviations and self-contamination during personal protective equipment donning and doffing", Infect Control Hosp Epidemiol. 2017;38(9). doi:10.1017/ice.2017.121, pp. 1077-1083.
Leung, N. H. L., "Respiratory virus shedding in exhaled breath and efficacy of face masks", Nat Med. 2020;26(5): doi:10.1038/s41591-020-0843-2, pp. 676-680.
Liao, L., "Can N95 respirators be reused after disinfection? How many times?", ACS Nano. 2020;14(5). doi:10.1021/acsnano.0c03597, pp. 6348-6356.
Lindsley, W. G., "Effects of ultraviolet germicidal irradiation (UVGI) on N95 respirator filtration performance and structural integrity", J Occup Environ Hyg. 2015;12(8). doi:10.1080/15459624.2015.1018518, pp. 509-517.
Liu, J., "Efficacy of slit lamp breath shields", Am J Ophthalmol. 2020;218. doi:10.1016/j.ajo.2020.05.005, pp. 120-127.
Lockhart, S. L., "Simulation as a tool for assessing and evolving your current personal protective equipment: lessons learned during the coronavirus disease (COVID-19) pandemic", Can J Anesth Can Anesth. 2020;67(7). doi:10.1007/s12630-020-01638-z, pp. 895-896.
Mattogno, p. P., "Transnasal endoscopic skull base surgery during COVID-19 pandemic: algorithm of management in an Italian reference COVID center", Acta Neurochir. 2020;162(8). doi:10.1007/s00701-020-04414-6, pp. 1783-1785.
McCarty, E. B., "Innovations in otorhinolaryngology in the age of COVID-19: a systematic literature review", World J Otorhinolaryngol Head Neck Surg. 2021:1-16. Epub ahead of print. doi:10.1016/j.wjorl.2021.01.001, pp. 224-238.
Narwani, V., "Application of a modified endoscopy face mask for flexible laryngoscopy during the COVID-19 pandemic", Otolaryngol Neck Surg. 2020;163(1). doi:10.1177/0194599820928977, pp. 107-109.
Patel, S. H., "Assessing the physiological relevance of cough simulators for respiratory droplet dispersion", J Clin Med. 2020;9(9):3002. doi:10.3390/jcm9093002, 11 pages.
Patel, Z. M., "Letter: precautions for endoscopic Transnasal Skull Base surgery during the COVID-19 pandemic", Neurosurgery. 2020;87. doi:10.1093/neuros/nyaa 125, pp. E66-E67.
Poostchi, A., "Efficacy of slit lamp breath shields", Eye. 2020;34(7). doi: 10.1038/s41433-020-0940-y, pp. 1185-1186.
Rameau, A., "Flexible laryngoscopy and COVID-19", Otolaryngol Neck Surg. 2020;162(6). doi: 10.1177/0194599820921395, pp. 813-815.
Schirmer, A., "Break scrub to take that phone call?", J Am Coll Surg. 2018;226(6). doi:10.1016/j.jamcollsurg.2018.03.002, pp. 1117-1121.
Seto, W. H., "Effectiveness of precautions against droplets and contact in prevention of nosocomial transmission of severe acute

(56) References Cited

OTHER PUBLICATIONS respiratory syndrome (SARS)", Lancet Lond Engl. 2003; 361(9368); doi:10.1016/S0140-6736(03)13168-6; pp. 1519-1520.
Shah, S. H., "Assessment of respiratory droplet transmission during the ophthalmic slit lamp exam: a particle tracking analysis", Am J Ophthalmol 2021;222. doi: 10.1016/j.ajo.2020.08.046, pp. 76-81.
Sickbert-Bennett, E. E., "Filtration efficiency of hospital face mask alternatives available for use during the COVID-19 pandemic", JAMA Intern Med. 2020;180. doi: 10.1001/jamainternmed.2020.4221, pp. 1607-1612.
Solari, D., "The nose lid for the endoscopic endonasal procedures during COVID-19 era: technical note", Acta Neurochir (Wien). 2020;162. doi: 10.1007/s00701-020-04518-z, pp. 2335-2339.
Thatiparti, D. S., "Computational fluid dynamics study on the influence of an alternate ventilation configuration on the possible flow path of infectious cough aerosols in a mock airborne infection isolation room", Sci Technol Built Environ. 2016;23(2). doi:10.1080/23744731.2016.1222212, pp. 355-366.
Vahabzadeh-Hagh, A.M., "Patient-worn endoscopy mask to protect against viral transmission", Laryngoscope Investigative Otolaryngology. 2022;7:190-196.
Van Doremalen, N., "Aerosol and surface stability of SARS-CoV-2 as compared with SARS-CoV-1", N Engl J Med. 2020;382(16):1564-1567. doi:10.1056/NEJMc2004973, 4 pages.
Vukkadala, N., "Covid-19 and the otolaryngologist: preliminary evidence-based review", The Laryngoscope. 2020;130: doi:10.1002/lary.28672, pp. 2537-2543.
Workman, A. D., "Endonasal instrumentation and aerosolization risk in the era of COVID-19: simulation, literature review, and proposed mitigation strategies", Int Forum Allergy Rhinol. 2020;10(7): doi:10.1002/alr.22577, pp. 798-805.
Zou, L., "SARS-CoV-2 viral load in upper respiratory specimens of infected patients", N Engl J Med. 2020;382: 1177-1179, doi:10.1056/NEJMc2001737, 3 pages.

* cited by examiner

Table 1.

| Sample | Polypropylene Sterilization Wrap | 3M N95 1860 |
|---|---|---|
| Filtration Efficiency | 97.31±0.32 | 96.52±1.37* |

Table 2.

| Metric | Mental Demand | Physical Demand | Temporal Demand | Performance | Effort | Frustration | Total NASA TLX Score | Time (s) |
|---|---|---|---|---|---|---|---|---|
| Average±Standard Deviation (mask) | 47.0±25.0 | 33.5±23.1 | 44.0±24.0 | 23.5±20.55 | 43.5±20.8 | 18.5±13.6 | 233.3±59.1 | 28.7±13.6 |
| Average±Standard Deviation (no mask) | 48.0±20.7 | 31.0±19.8 | 48.0±20.4 | 18.0±11.4 | 45.5±22.3 | 17.0±13.0 | 229.44±53.5 8 | 27.8±8.0 |
| p-value | 0.82 | 0.46 | 0.32 | 0.19 | 0.63 | 0.76 | 0.76 | 0.41 |

*FIG. 8*

ENDOSCOPY MASK WITH AIR FILTRATION

CROSS REFERENCE TO RELATED APPLICATION

This patent document is a U.S.C. § 371 National Stage application of International Application No. PCT/US2021/058120 titled "ENDOSCOPY MASK WITH AIR FILTRATION" and filed on Nov. 4, 2021, which claims the benefit of priority to U.S. Provisional Patent Application No. 63/110,316, titled "ENDOSCOPY MASK WITH AIR FILTRATION," filed on Nov. 5, 2020. The entire content of the before-mentioned patent applications is incorporated by reference as part of the disclosure of this document.

TECHNICAL FIELD

This patent document relates to personal protective equipment (PPE) for patients and physicians and in particular a protective mask for procedures in the nose and mouth.

BACKGROUND

During many medical procedures, patients and physicians share a common breathing space where respiratory droplets from the patient and/or physician may be ejected into the shared airspace exposing the other to the respiratory droplets. Respiratory droplets can also contaminate surfaces and equipment. During some procedures, the physician must have access to the patient's nose and/or mouth in order to perform a procedure. New devices are needed to protect both the physician and the patient from exposure to respiratory droplets to prevent the spread of illnesses including the flu and COVID-19.

SUMMARY

Disclosed is an apparatus for providing air filtration between a doctor or health care provider and a patient during nose and mouth medical procedures including endoscopic procedures, and methods of providing air filtration in a medical exam room. In one aspect a medical mask apparatus is disclosed. The medical mask includes a mask material conforming to a patient's face along a sealing surface. The medical mask further includes a nose cone with a conically shaped first end and a cylindrically shaped second end, a cap that engages the second end of the nose cone through the mask material, wherein a portion of the mask material is captured at an interface between the nose cone and the cap. There is a valve in the cap, wherein the valve is flexible to expand and allow a medical instrument to pass through the valve. The medical mask also includes one or more attachment straps to hold the medical mask apparatus on the patient's face. The medical mask can include one or more of the following features. The mask material provides N95 or HEPA air filtration between a patient side of the mask and an examination room side of the mask. The mask material is produced form woven polypropylene or polyethylene. The nose cone and the cap comprise a natural or synthetic rubber, a silicone, or a plastic material. The valve is produced using a silicone material or a natural or synthetic rubber material. The medical instrument is an endoscope. The medical mask can further include a malleable nose bridge attached to the mask material to cause the mask material to conform to a shape of a nose bridge.

In another aspect, a method of providing a sterile environment in a medical exam room for an endoscopy in a patient's nose or mouth is disclosed. The method includes applying a medical mask to the patient, wherein the medical mask comprises: a mask filtration material conforming to the patient's face along a sealing surface, and a valve providing an opening capable of passing an endoscope through the port and into the patient's nose or mouth. The method further includes inserting an endoscope through the valve of the medical mask. The method can include one or more of the following features. The method can further include performing the endoscopy and removing, after the endoscopy, the medical mask. The mask material provides N95 of HEPA air filtration between a patient side of the mask to an examination room side of the mask. The mask material is produced form woven polypropylene or polyethylene. The nose cone has a conically shaped first end and a cylindrically shaped second end, wherein the cap engages the second end of the nose cone through the mask material, wherein a portion of the mask material is captured at an interface between the nose cone and the cap, wherein the cap includes the valve. The valve is flexible to expand and allow endoscopic instrument or other instrument to pass through the valve. The nose cone and the cap comprise a natural or synthetic rubber, a silicone, or a plastic material. The valve comprises a silicone material or a natural or synthetic rubber material. A malleable nose bridge is attached to the mask material to cause the mask material to conform to the shape of a nose bridge, wherein the malleable nose bridge comprises a metal.

BRIEF DESCRIPTION OF THE DRAWINGS

FIG. 8 shows a table showing an example of filtration efficiency and another table showing that the effort required by a physician using the disclosed mask is no greater than when no mask is used.

DETAILED DESCRIPTION

Figure 1:
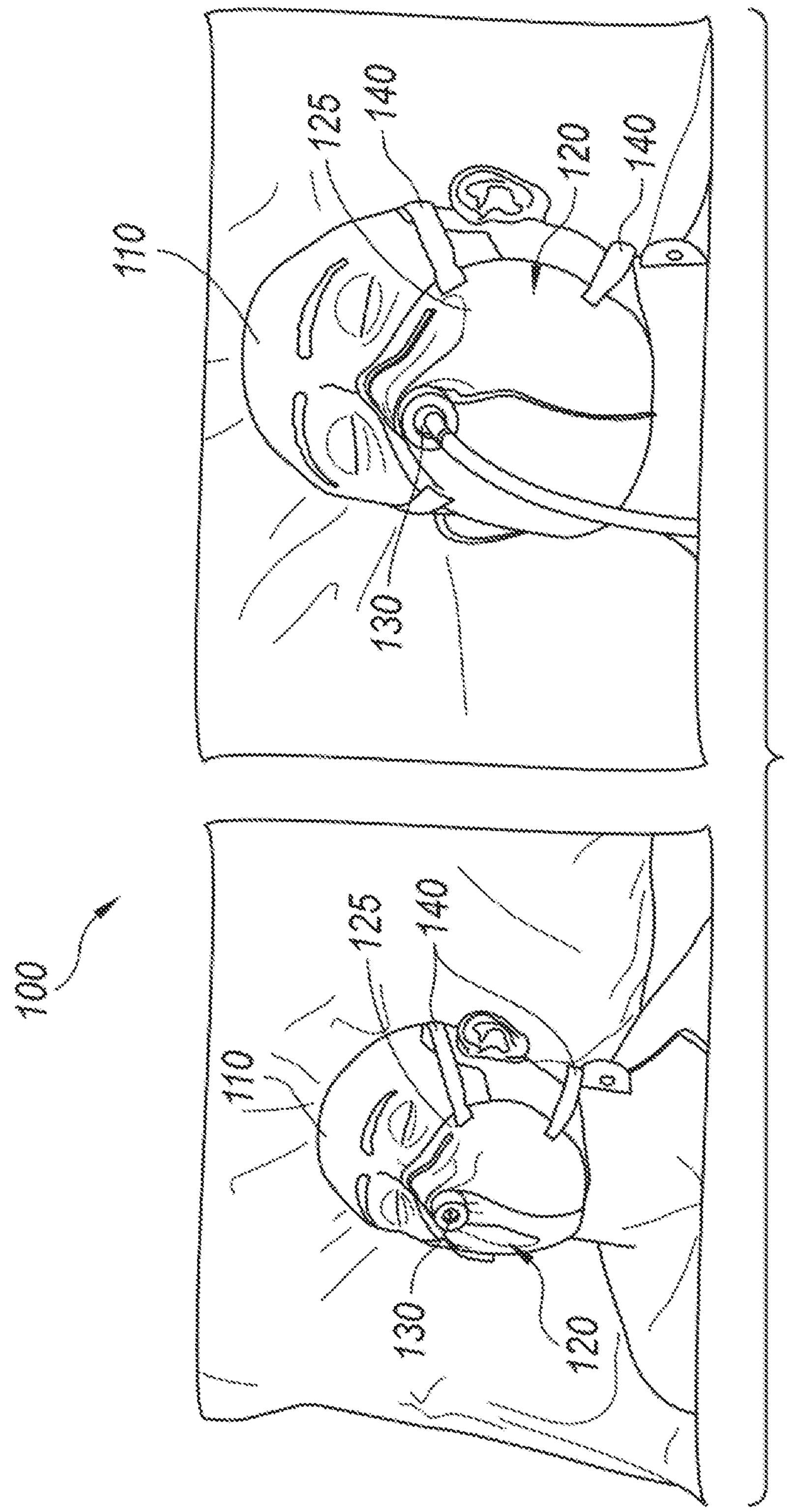
FIG. 1 shows an example diagram of a patient wearing a mask with air filtration for nose, mouth, and other medical procedures.

Many medical procedures require that the physician have access to the patient's nose and/or mouth. For example, trans-nasal endoscopy is a procedure in which a thin camera is inserted into the nose in order to visualize internal anatomy. During trans-nasal endoscopy, patients are often awake and may sneeze or cough thereby ejecting respiratory droplets and aerosol matter out of the patient and into the breathing space the patient shares with the physician and staff who are usually less than three feet away. Thus, there is a risk of aerosol matter and respiratory droplets being ejected by the patient posing a risk to the physician and staff of contracting an illness such as the flu, COVID-19, or another illness caused by airborne particles such as viruses, organisms such a bacteria, or other biological or non-biological materials.

Disclosed is a mask providing air filtration through the surface of the mask that allows for the insertion of an endoscope into the patient's nose or mouth. A nose cone passes from the inside of the mask, through an opening in the mask material to the outside of the mask where a cylindrical portion of the nose cone couples to a cap on the outside of the mask. Mask material is squeezed between the nose cone and cap to maintain the filtration capability of the mask by only allowing air to pass through the mask material.

Masks and respirators provide air filtration. For example, N95 respirators filter 95% or more of 0.3 μm particles and are the mainstay of protection against airborne pathogens. Airborne transmission of some illnesses results from contact with infectious particles contained within small (<5 μm) droplet nuclei (i.e., aerosols) that can linger in the air for hours and be dispersed over large distances. Other pathogens such as SARS-CoV-2 are primarily spread by larger (>5-~10 μm) respiratory droplets that can be expelled up to six feet horizontally and drop to the ground within seconds. In various embodiments of the disclosed subject matter, different filtration capabilities may be provided by selecting different filtration materials. For example, N95 filtration can be provided, or filtration of smaller or larger particles with more than 95%, or less than 95% efficiency depending on the protection needs as well as other requirements such as cost. In another example, HEPA air filters remove at least 99.95% (European standard) or 99.97% (U.S. standard) of particles whose diameter is equal to 0.3 μm with a filtration efficiency increasing for particle diameters both less than and greater than 0.3 μm. For the disclosed mask, the mask material includes materials such as polypropylene, polyethylene, a high-efficiency particulate air (HEPA) filter material (European or U.S. standard), other HEPA material, or a N95 filtration material, or other filtration material.

Masks may be constructed of a flexible material that provides filtration through the flexible material such as woven polypropylene or other filtration material as described above that makes up the mask. On the other hand, respirators may be made of a non-permeable material such as plastic or rubber that direct airflow through a filter that is attached to an opening in the respirator such as being threaded into a receptacle in the plastic/rubber respirator. The following describes a protective mask but the disclosed techniques can be used for a respirator as well.

In some example embodiments, a mask is disclosed that maintains N95 filtration efficacy while allowing insertion of a flexible or rigid endoscope to permit safe endoscopic evaluation of patients without the risk of disease transmission via aerosol droplets. Use of the mask allows safe endoscopic evaluation of patients and reduces disease transmission from the patient to the provider and from the provider to the patient and reduces contamination of examination room areas thereby reducing transmissibility to others in the vicinity of the examination room or subsequently occupy the same exam space. The mask maintains a seal around a patient's facial structure. The mask has a port that is sealed before use and provides a seal around an endoscope that has been inserted through a port in the mask. The port accommodates endoscopes that are flexible or rigid and of variable diameters. For example, endoscopes with a diameter of 2 mm or larger including endoscopes with a diameter of 6 mm can be accommodated as well as larger and smaller diameter endoscopes.

The disclosed mask can be worn by a patient during trans-nasal endoscopy, trans-oral endoscopy, as well as other procedures. The mask material provides filtration such as N95 filtration efficiency and the mask has a port through which the endoscope can be inserted. The port includes a nose cone and a cap to allow entrance of an endoscope into the mask and later the patient. The nose cone also provides an end piece that can enter, stabilize, and facilitate entrance of the endoscope into the nose or mouth. The endoscope port articulates with the nostril or lips to provide a stable conduit for entrance into the nose or mouth. The disclosed port facilitates an endoscopy and may reduce the time needed to perform the endoscopy by making one of the more difficult parts which is entrance into the natural orifice (e.g., nose, mouth) easy and painless for the patient.

A patient will put on the mask at the time of the procedure or an earlier time to provide filtration protection before the procedure. Air filtration continues from the time the patient puts the mask on until after the procedure when the patient takes the mask off. When the provider or physician is ready, the provider may ask the patient to move the nose cone into a nostril, or the provider will insert the nose cone into a nostril. This is done by moving the external cap that is connected to the nose cone to guide the nose cone into a nostril. The provider can also change the nostril in which the nose cone enters by sliding it into the adjacent nostril. They may also insert the endoscope up to the tip of the nose cone first, and then insert it into the nose since this will allow internal visualization in additional to tactical feedback to the provider. Once correctly positioned, the provider will insert the endoscope through a valve on the cap and slide it through and into the nose as they would during a regular procedure. The valve may be made of a flexible silicone or other flexible material. A lubricant may be used in order to reduce the amount of frictional force from the endoscope-silicone interface. In some example embodiments, the nose cone is conical at the end that is inserted into a patient's nose. In other embodiments, the nose cone can be a different shape such as cylindrical at the end that enters the nose.

Once the provider has finished the procedure, they will pull the endoscope out as they normally do. The mask can be taken off by the patient at that time or a later time to continue to provide protective air filtration.

The disclosed device may be used in any clinical setting that performs endoscopies including trans-oral or trans-nasal endoscopies performed by physicians specializing in ear nose and throat (ENT), pulmonary, gastroenterology, oncology, and so on as well as outpatient procedures and surgeries. The disclosed device can be used on mildly sedated or conscious patients.

FIG. 1 at 100 shows a patient 110 wearing a filtration mask 120 which includes port 130 to insert an instrument such as endoscope 150 into the patient's nose or mouth. Mask 120 is held onto the face of patient 110 via straps 140. Port 130 passes through mask 120 via an opening in the mask material 125 through which a nose cone attaches to a cap that seals the opening.

Figure 2:
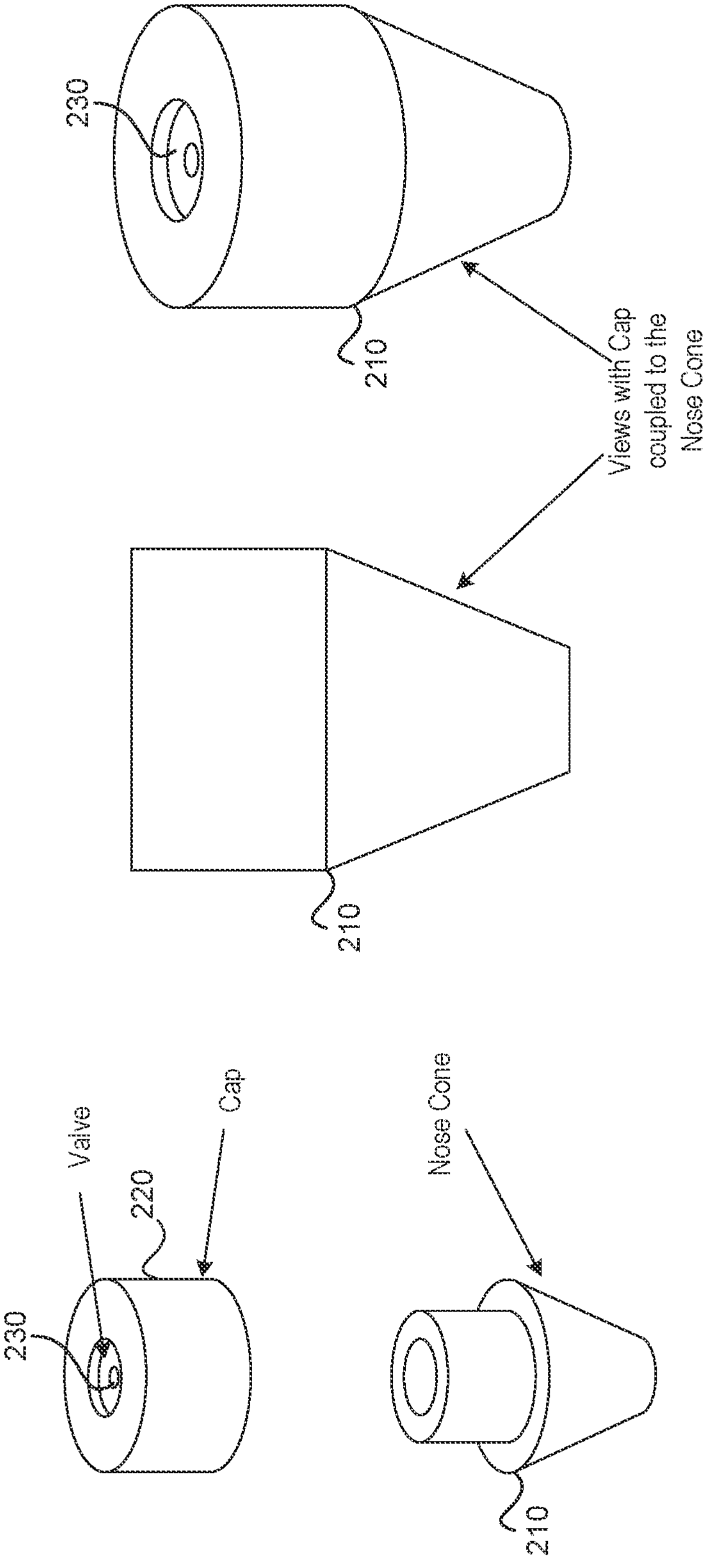
FIG. 2 shows an example nose cone and cap for a mask with air filtration.

FIG. 2 shows at 200 an example of a port including a nose cone 210 and a cap 220. Nose cone 210 can have a tapered, conical, cylindrical, or other shape at a first end and a cylindrical shape at a second end. The cylindrically shaped second end can be press fit into cap 220. Cap 220 includes a valve 230 made of flexible material with a small hole in the middle that allows for an endoscope or other medical tool to pass through. Insertion of the endoscope or other tool causes the valve 230 to stretch in its inner diameter to allow the device to pass through the valve. The cylindrical second end of nose cone 210 passes through a hole in the mask material (not shown in FIG. 2). Some of the mask material is captured in the interface between the nose cone 210 and cap 220 when the nose cone 210 is pressed into cap 220 prior to use. In some example embodiments, such as in the manufacture of disposable filtration masks, the nose cone may be pressed through the mask material and into the cap at the time of manufacture. In other embodiments, the nose cone and cap may be reusable, and the filtration mask material may be disposable. In these embodiments, the nose cone 210 may be pressed through the mask material and into cap 220 in the physician's office or treatment room prior to use.

In some example embodiments, the nose cone and cap can be a single element or single piece of material that passes through the mask material where the cap and nose cone are not pressed together or are pressed together before placing the nose cone/cap into the mask material. For example, the mask material or a separate seal can provide a seal between the mask material and the nose cone/cap element.

In some example embodiments, the nose cone and cap can have a unibody construction, can be press fitted together, riveted, lure locked, threaded and screwed together, and so on. Different diameters of nose cones, different diameters of the port (cap and nose cone), different diameters for the cap, and/or different diameters for the valve can be used.

The nose cone 210 and cap 220 may be made of the same or different materials. For example, the nose cone 210 and cap 220 may be made from plastic or rubber, silicone, polycarbonate, polylactide (PLA), nylon, acrylonitrile butadiene styrene (ABS) plastic, polyethylene terephthalate glycol (PETG), polyvinyl chloride (PVC), polypropylene, high impact polystyrene, poly(vinyl chloride) plastisol (PVCP), latex, natural and synthetic rubbers, steel, aluminum, or other material. Valve 230 may be made from silicone or other flexible, expandable, or elastic material.

Figure 3:
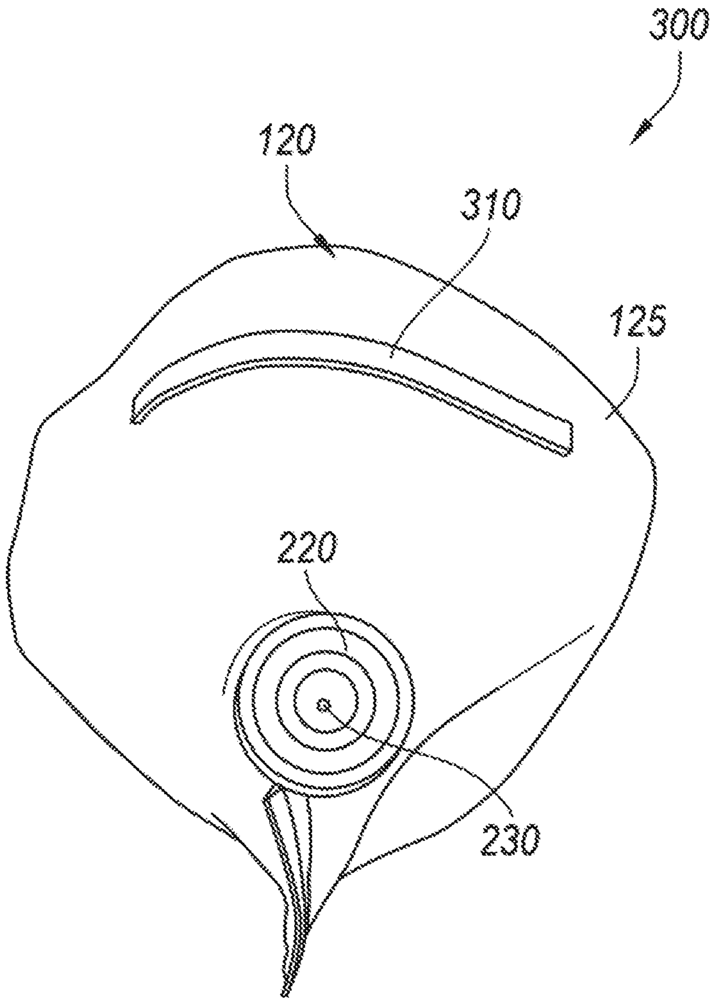
FIG. 3 shows an example outside view of a mask with air filtration.

FIG. 3 shows an example diagram 300 of the outside of a filtration mask. Attached to mask material 125 is bridge 310 made of malleable material to cause material 125 to conform to the shape of a patient's nose bridge. Cap 220 and valve 230 are also shown.

Figure 4:
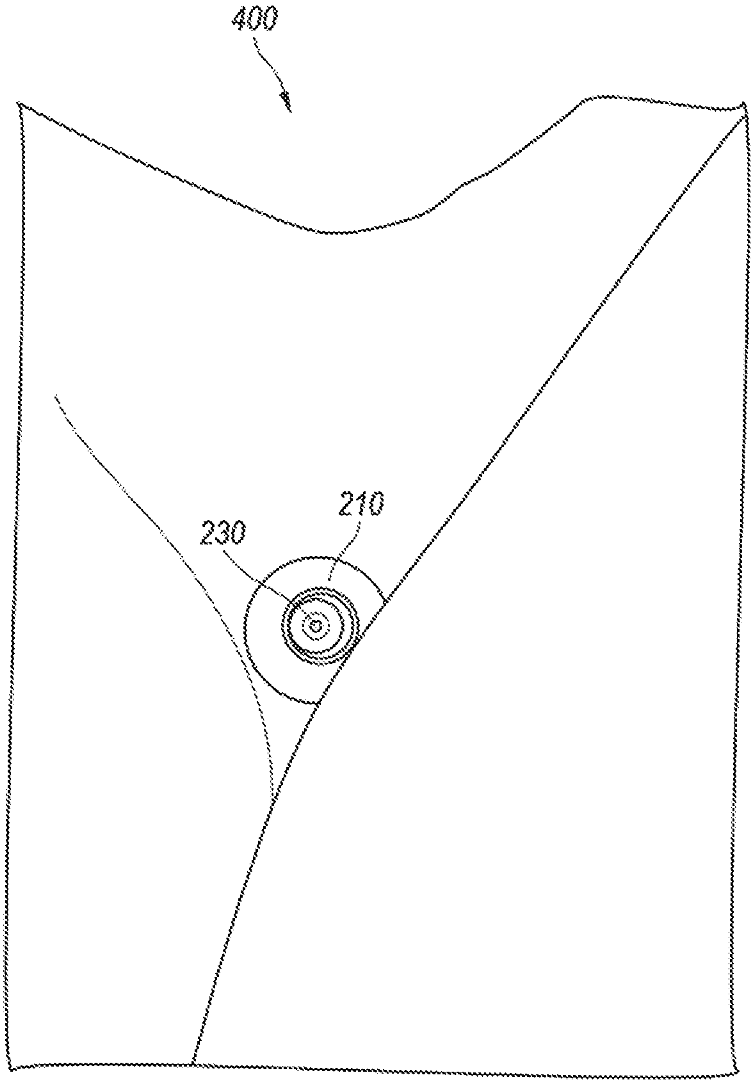
FIG. 4 shows an example inside view of a mask with air filtration.

FIG. 4 shows an example diagram 400 of the inside of a filtration mask. Nose cone 210 is visible and passes through mask material 125 to engage cap 220 (not shown). Valve 230 is also shown.

Figure 5:
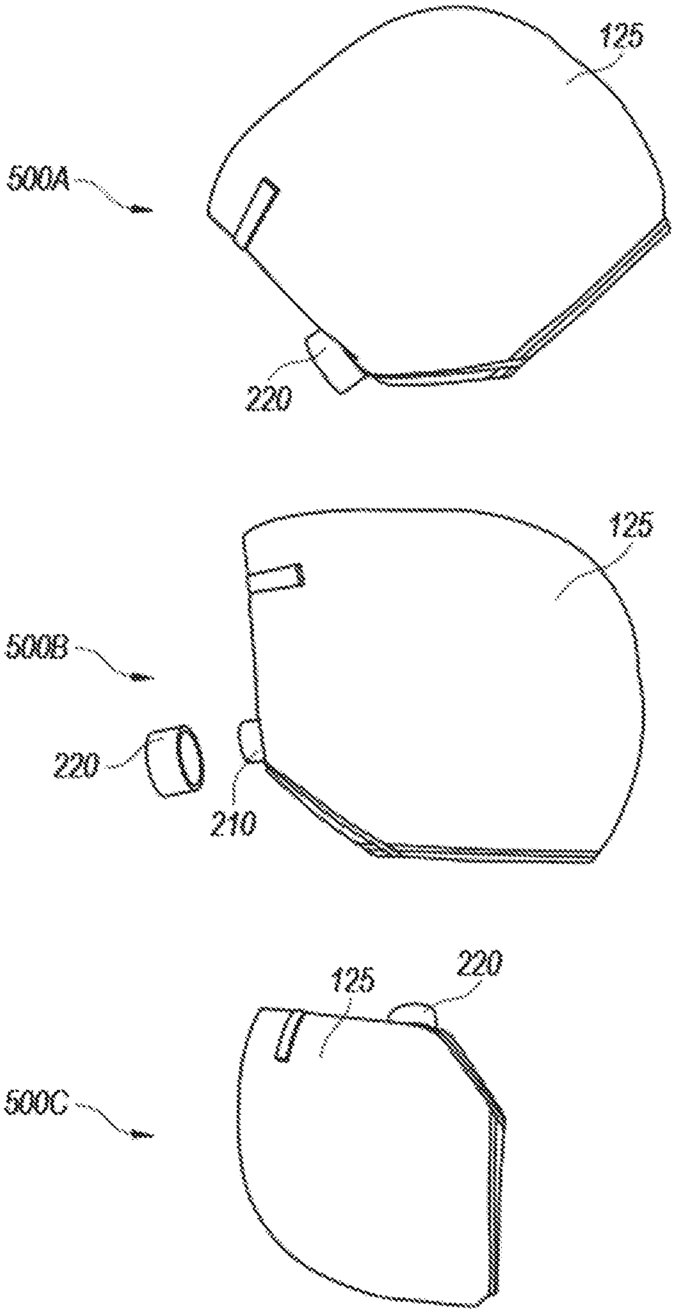
FIG. 5 shows example side views of a mask with air filtration.

FIG. 5 shows side views 500A-500C of a filtration mask. Views 500A and 500C show mask material 125, cap 220, and bridge 310. View 500B shows cap 220 disengaged from the cylindrical end of nose cone 210.

Figure 6:
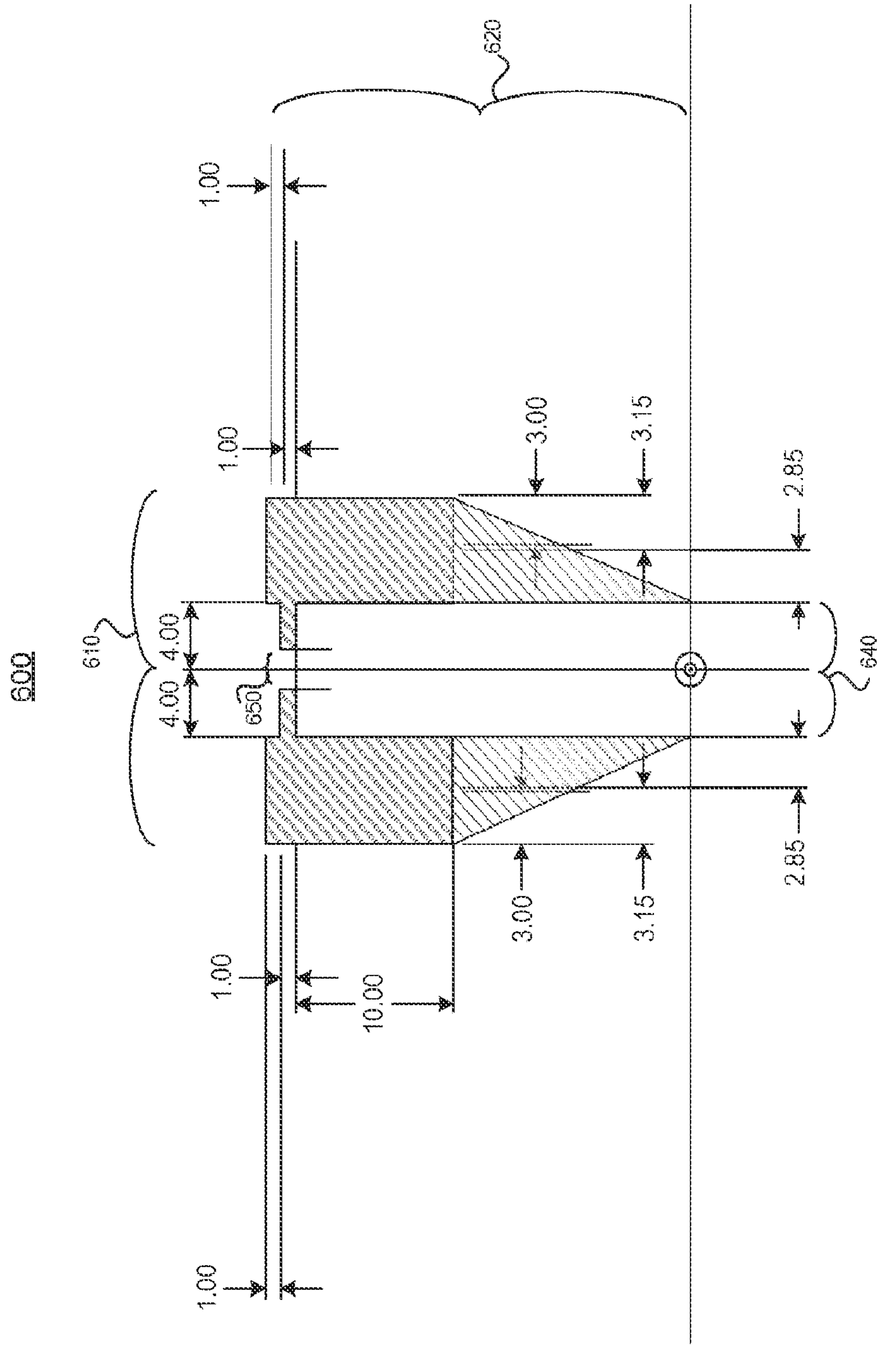
FIG. 6 shows a drawing of a nose cone with example dimensions.

FIG. 6 shows an example drawing of a nose cone. Example dimensions for the various aspects are shown in millimeters. Nose cones with different dimensions are also possible. Shown in FIG. 6 at 610 is a nose cone diameter of 20 mm that tapers to a diameter of 8 mm at 640, the narrowest part of the cone which is designed to be placed into a patient's nostril. In the example of FIG. 6, the nose cone has an overall height of shown at 620. In the example of FIG. 6, the valve has an outer diameter shown at 640 of 8 mm and an inner diameter shown at 650 of 2 mm. In the example of FIG. 6, the valve is made from the same material as the nose cone and has a thickness of 1 mm. In some other example embodiments, the valve can be a separate device that is inserted into the nose cone. The separate valve can be made from a different material from the nose cone material. In this case, the top of the nose cone at the valve 640 can have a different diameter (e.g., 8 mm) to accommodate the separately produced valve.

Figure 7:
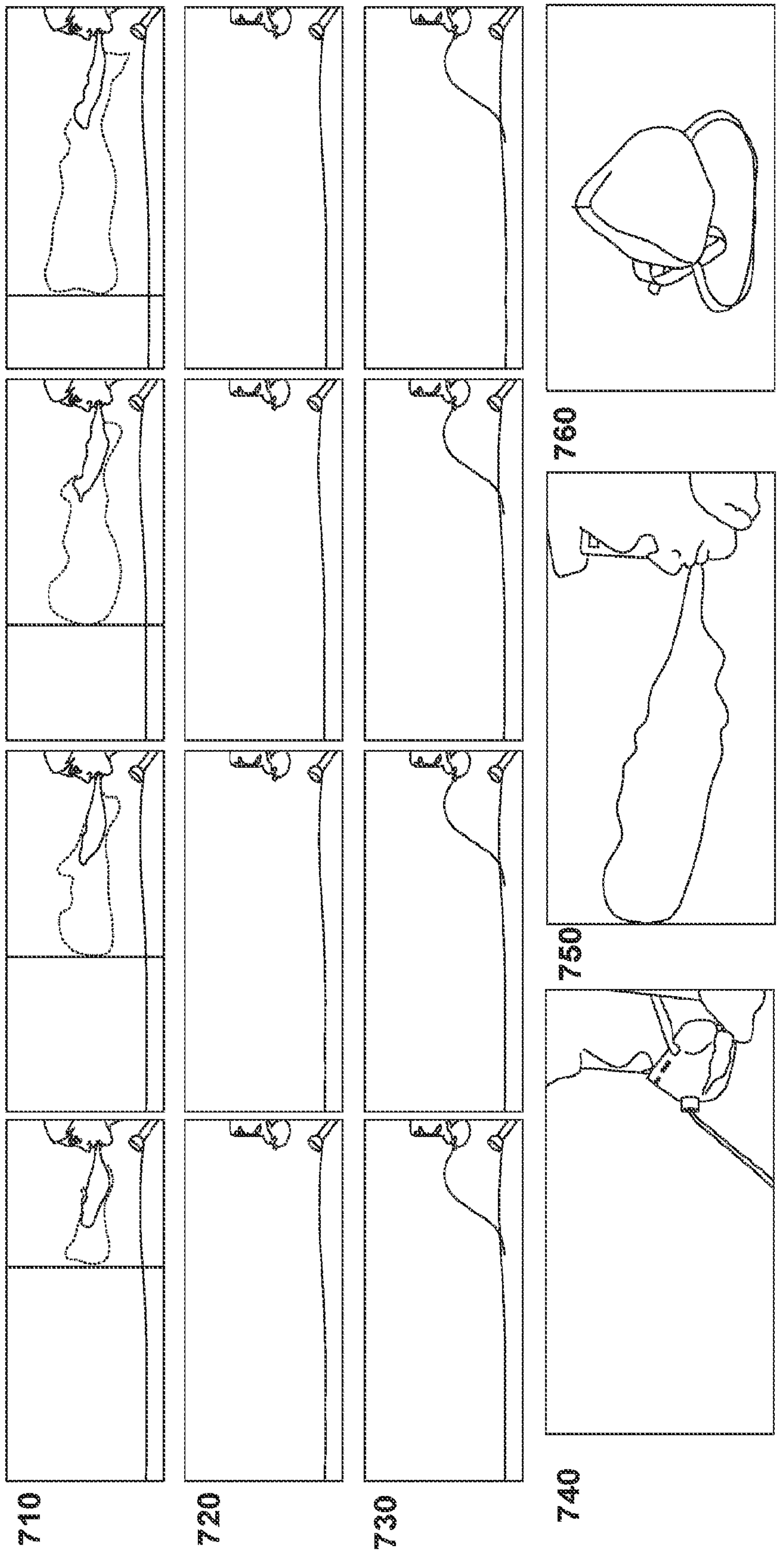
FIG. 7 shows example diagrams showing droplet spray patterns from a patient's cough and the absence of a spray pattern when a patient is wearing the disclosed mask.

FIG. 7 shows example diagrams showing the containment effects of a mask. At 710, four progressive diagrams are shown (from left to right with increasing time) from a single simulated cough with no mask being worn. The outlines indicate the farthest distance the cough plume travels at the time corresponding to each image. As shown at 710, generally as time progresses, the cough plume has traveled farther from the patient and spreads out. At 720, four progressive diagrams are shown from a single simulated cough with a mask consistent with the disclosed subject matter being worn without an endoscope or instrument inserted into the cap valve. As can be seen in 720 almost no cough plume, or no cough plume, emanates from the patient. At 730, four progressive diagrams are shown from a single simulated cough with a mask consistent with the disclosed subject matter being worn with an endoscope or instrument inserted into the cap valve. As can be seen in 730, similar to 720 almost no cough plume, or no cough plume, emanates from the patient. At 740, a close-up diagram is shown of a mask being worn and an instrument inserted during a simulated cough. Similar to the diagrams at 720 and 730, almost no cough plume, or no cough plume, emanates from the patient. At 750, a close-up image is shown from a simulated cough with no mask being worn. As can be seen at 750, a cough plume emanates from the patient when no mask is worn. At 760, a diagram shows the inside of the mask with a scope inserted into the mask.

FIG. 8 at Table 1 shows a comparison of filtration efficiency between an N95 material (3M N95 1860) and a polypropylene sterilization wrap material. Very similar filtration efficiencies are shown for the two materials. Table 2 shows various usability metrics fora physician performing an endoscopic procedure on a patient without a mask and a patient wearing a mask consistent with the disclosed subject matter. These metrics include mental demand, physical demand, temporal demand, performance, effort, frustration, a total NASA TLX score, and time. The p-value indicates the probability of obtaining test results at least as extreme as the results actually observed. Table 2 shows that a procedure on a patient wearing the mask has comparable physician difficulty to a procedure on a patient not wearing the mask.

Figure 9:
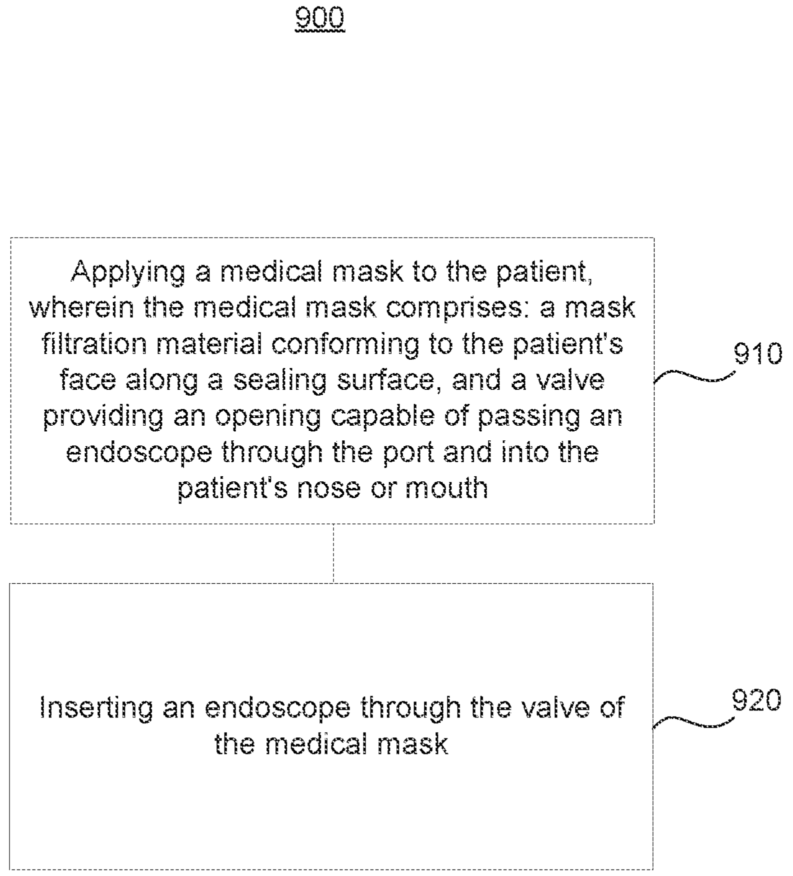
FIG. 9 depicts a method, in accordance with some example embodiments.

FIG. 9 shows an example of a process, in accordance with some example embodiments. The method provides for a sterile environment in a medical exam room for performing an endoscopy in a patient's nose or mouth. The method includes applying a medical mask to the patient, wherein the medical mask includes: a mask filtration material conforming to the patient's face along a sealing surface, and a valve providing an opening capable of passing an endoscope through the port and into the patient's nose or mouth. The method further includes inserting an endoscope through the valve of the medical mask.

In some example embodiments, the mask material provides N95 of HEPA air filtration between a patient side of the mask to an examination room side of the mask. The mask material can be produced form woven polypropylene or polyethylene. The nose cone may have a conically shaped first end and a cylindrically shaped second end, wherein the cap engages the second end of the nose cone through the mask material. A portion of the mask material can be captured at an interface between the nose cone and the cap. The cap may include the valve where the valve is flexible to expand and allow an endoscope or other instrument to pass through the valve. The nose cone and cap can be produced using a natural or synthetic rubber, silicone, or a plastic material. The valve can be produced using a silicone material or a natural or synthetic rubber material. A malleable nose bridge can be attached to the mask material to cause the mask material to conform to the shape of a nose bridge.

Although a few variations have been described in detail above, other modifications or additions are possible. In particular, further features and/or variations may be provided in addition to those set forth herein. Moreover, the example embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

Similarly, while elements are depicted in the drawings in a particular order, this should not be understood as requiring that the elements be assembled or performed in the particular order shown or in sequential order, or that all illustrated operations be performed, to achieve desirable results. Moreover, the separation of various elements in the embodiments described in this patent document should not be understood as requiring such separation in all embodiments.

Only a few implementations and examples are described and other implementations, enhancements and variations can be made based on what is described and illustrated in this patent document.

What is claimed is:

1. A medical mask apparatus, comprising:

a mask material configured to conform to a patient's face along a sealing surface;

a nose cone with a conically shaped first end and a cylindrically shaped second end;

a cap that engages the second end of the nose cone through the mask material, wherein a portion of the mask material is captured at an interface between the nose cone and the cap;

a valve in the cap, wherein the valve is flexible to expand and allow a medical instrument to pass through; and one or more attachment straps configured to hold the medical mask apparatus on the patient's face.

2. The medical mask apparatus of claim 1, wherein the mask material provides N95 or HEPA air filtration between a patient side of the medical mask apparatus and an examination room side of the medical mask apparatus.

3. The medical mask apparatus of claim 1, wherein the mask material comprises woven polypropylene or polyethylene.

4. The medical mask apparatus of claim 1, wherein at least one of the nose cone or the cap comprises a natural or synthetic rubber, a silicone, or a plastic material.

5. The medical mask apparatus of claim 1, wherein the valve comprises a silicone material or a natural or synthetic rubber material.

6. The medical mask apparatus of claim 1, wherein the medical instrument comprises an endoscope.

7. The medical mask apparatus of claim 1, further comprising:

a malleable nose bridge attached to the mask material to cause the mask material to conform to a shape of a nose bridge of the patient.

8. The medical mask apparatus of claim 7, wherein the malleable nose bridge comprises a metal.

9. A method of providing a sterile environment in a medical exam room for an endoscopy in a patient's nose or mouth, the method comprising:

applying a medical mask to the patient, wherein the medical mask comprises:

a mask material configured to conform to the patient's face along a sealing surface, a nose cone with a conically shaped first end and a cylindrically shaped second end, a cap configured to engage the second end of the nose cone through the mask material, a portion of the mask material being captured at an interface between the nose cone and the cap, and a valve, in the cap configured to provide an opening capable of passing an endoscope through and into the patient's nose or mouth; and inserting an endoscope through the valve of the medical mask.

10. The method of claim 9, further comprising:

performing the endoscopy; and removing, after the endoscopy, the medical mask.

11. The method of claim 9, wherein the mask material provides N95 or HEPA air filtration between a patient side of the medical mask to an examination room side of the medical mask.

12. The method of claim 9, wherein the mask material comprises woven polypropylene or polyethylene.

13. The method of claim 9, wherein the valve is flexible to expand and allow the endoscope or other instrument to pass through.

14. The method of claim 9, wherein the medical mask comprises a nose cone and a cap, and wherein at least one of the nose cone or the cap comprises a natural or synthetic rubber, a silicone, or a plastic material.

15. The method of claim 9, wherein the valve comprises a silicone material or a natural or synthetic rubber material.

16. The method of claim 9, wherein a malleable nose bridge is attached to the mask material to cause the mask material to conform to the shape of a nose bridge of the patient.

17. The method of claim 16, wherein the malleable nose bridge comprises a metal.

* * * * *